United States Patent
Hatahori et al.

(10) Patent No.: US 9,551,617 B2
(45) Date of Patent: Jan. 24, 2017

(54) RAMAN SPECTROSCOPIC ANALYZER

(71) Applicant: SHIMADZU CORPORATION, Kyoto-shi, Kyoto (JP)

(72) Inventors: Takahide Hatahori, Osaka (JP); Naoji Moriya, Nara (JP)

(73) Assignee: SHIMADZU CORPORATION, Kyoto (JP)

( * ) Notice: Subject to any disclaimer, the term of this patent is extended or adjusted under 35 U.S.C. 154(b) by 0 days.

(21) Appl. No.: 14/903,530

(22) PCT Filed: Jun. 17, 2014

(86) PCT No.: PCT/JP2014/066019
§ 371 (c)(1),
(2) Date: Jan. 7, 2016

(87) PCT Pub. No.: WO2015/005075
PCT Pub. Date: Jan. 15, 2015

(65) Prior Publication Data
US 2016/0146668 A1 May 26, 2016

(30) Foreign Application Priority Data
Jul. 11, 2013 (JP) .................................. 2013-145360

(51) Int. Cl.
*G01J 3/44* (2006.01)
*G01N 21/05* (2006.01)
(Continued)

(52) U.S. Cl.
CPC ................ *G01J 3/44* (2013.01); *G01J 3/0218* (2013.01); *G01J 3/0224* (2013.01); *G01N 21/05* (2013.01); *G01N 21/65* (2013.01)

(58) Field of Classification Search
CPC .............. G01J 3/44; G01J 3/0218; G01J 3/02; G01J 3/28
(Continued)

(56) References Cited

U.S. PATENT DOCUMENTS

| 6,177,984 | B1 * | 1/2001 | Jacques | ................. G01J 4/00 356/338 |
| 8,427,644 | B2 * | 4/2013 | Miki | ................. G01B 11/026 356/364 |
| 2014/0118731 | A1 * | 5/2014 | Ayers | ................. G01J 3/0237 356/301 |

FOREIGN PATENT DOCUMENTS

JP 2011-80768 A 4/2011

OTHER PUBLICATIONS

Written Opinion for PCT/JP2014/066019 dated Sep. 16, 2014. [PCT/ISA/237].

* cited by examiner

Primary Examiner — Abdullahi Nur
(74) Attorney, Agent, or Firm — Sughrue Mion, PLLC

(57) ABSTRACT

Raman spectroscopic analyzer including: a beam-casting unit 3 for receiving a light beam generated by a light source and for converging the light beam on a predetermined position in a perpendicular direction to the longitudinal direction of a measurement chamber through which a liquid sample is passed; and a light-receiving unit placed at a distance in the longitudinal direction from the predetermined position, for receiving scattered light emitted from the fluid sample. Among the scattered light which enters the light-receiving unit, the portion which enters this unit after being reflected by the inner wall surface opposite to this unit is eliminated, so that the amount of noise in the Raman spectroscopic measurement is considerably reduced.

8 Claims, 3 Drawing Sheets

(51) Int. Cl.
*G01N 21/65* (2006.01)
*G01J 3/02* (2006.01)

(58) Field of Classification Search
USPC .................................................. 356/300–344
See application file for complete search history.

RAMAN SPECTROSCOPIC ANALYZER

CROSS REFERENCE TO RELATED APPLICATIONS

This application is a National Stage of International Application No. PCT/JP2014/066019, filed Jun. 17, 2014, claiming priority based on Japanese Patent Application No. 2013-145360, filed Jul. 11, 2013, the contents of all of which are incorporated herein by reference in their entirety.

TECHNICAL FIELD

The present invention relates to a Raman spectroscopic analyzer for analyzing a component contained in a fluid sample (gas or liquid sample) using Raman-scattered light emitted from the sample.

BACKGROUND ART

An apparatus for analyzing a component in a sample by performing a Raman spectroscopic measurement normally includes a light source for generating the light to be cast into the sample (excitation light), an entrance optical system for converging the excitation light and casting it into the sample, a dispersing optical system for collecting the Raman-scattered light resulting from an interaction with a substance in the sample and dispersing the light into a spectrum, as well as a detector for detecting the component wavelengths of the light dispersed by the dispersing optical system.

If the intensity of the light from the sample is plotted on a graph with the wavelength as the abscissa and the intensity as the coordinate, a Raman scattering spectrum is obtained on both sides of the wavelength of the excitation light. The lines at the longer wavelengths are called the Stokes lines, and those at the shorter wavelengths are called the anti-Stokes lines.

The amount of energy corresponding to the difference between the wavelength of the excitation light and that of a Stokes or anti-Stokes line reflects the amount of energy of the natural vibration of a molecule. Accordingly, by calculating this amount of energy, it is possible to identify a substance in the sample. Furthermore, based on the intensity of each Stokes or anti-Stokes line appearing in the Raman scattering spectrum, the quantity of the substance corresponding to that Stokes or anti-Stokes line can be determined.

Patent Literature 1 discloses a gas component analyzer which identifies the components in a gas generated within a gasifying furnace and measures the concentration of each component by performing a Raman spectroscopic measurement.

FIG. 1 shows the configuration of the main components of this apparatus. In this gas component analyzer 100, laser light is cast into a stream of gas flowing in the direction perpendicular to the drawing within a tubular sample-passing unit 110 provided within the area surrounded by the broken line in a measurement chamber 115, and the Raman-scattered light emitted from the gas is measured. The laser light generated by a laser-casting device 114 controlled by a controller 137 is guided through a first optical fiber 120 into a light-casting means 116 and is converged on a predetermined position within the measurement chamber 115 by a lens 125 provided in the light-casting means 116. After passing through the gas, the laser light is disposed of at a damper 128.

Additionally, a detection optical system is provided on the wall of the measurement chamber 115 located in a direction perpendicular to the path of the laser light with respect to the aforementioned predetermined position. Among the Raman-scattered light emitted from the gas illuminated with the excitation laser light, the portion of light emitted in the perpendicular direction to the path of the laser light passes through alight-passing window 129 and is converged on a light-receiving unit 132 by a condensing lens 130. The light incident on the light-receiving unit 132 is guided through a second optical fiber 121 and is separated into component wavelengths by a light-dispersing device 135, to be eventually detected by a CCD camera 136.

CITATION LIST

Patent Literature

Patent Literature JP 2011-80768 A

SUMMARY OF INVENTION

Technical Problem

In the gas component analyzer described in Patent Literature 1, the laser light which has passed through the gas is absorbed by the damper 128. However, until it arrives at this damper, the light is scattered by the substances present on the optical path (e.g. the lens 125 of the light-casting means 116 or the gas present on the light path), and a portion of this scattered light is directed toward the light-passing window 129. Furthermore, the light scattered on the optical path is additionally reflected or scattered by the inner wall surface of the measurement chamber 115 and eventually falls onto the light-passing window 129. These forms of scattered light are also received by the light-receiving unit 132 together with the Raman-scattered light emitted from the gas.

In general, the Raman-scattered light emitted from gas has low intensities. Therefore, the scattered light which additionally originates from the excitation laser light enters the light-receiving unit 132 together with the Raman-scattered light constitutes a noise factor in the Raman spectroscopic analysis, which eventually deteriorates the accuracy in the identification of the components in the sample gas as well as the determination of the concentration of each component.

Although the previously described example is concerned with the case where the sample is in a gas form, a similar problem also occurs in the case of a measurement of the Raman-scattered light emitted from a liquid sample passing through the measurement chamber.

The problem to be solved by the present invention is to reduce the amount of noise resulting from the scattering of the excitation light in a Raman spectroscopic analyzer which detects Raman-scattered light emitted from a sample passing through a measurement chamber.

Solution To Problem

The Raman spectroscopic analyzer according to the present invention developed for solving the previously described problem includes:

a) a sample-passing unit in the form of a tube, for passing a fluid sample in a longitudinal direction of the tube;

b) a beam-casting unit for converging a light beam generated by a light source on a predetermined position within the sample-passing unit; and c) a light-receiving unit placed at a distance in the longitudinal direction from the predetermined position, including a light-receiving lens for receiving scattered light emitted from the fluid sample.

In a preferable mode of this analyzer, no inner wall surface of the sample-passing unit is present opposite to the light-receiving lens across the predetermined position. "No inner wall surface is present" means that no inner wall surface is present within a predetermined range of distances where the stray light caused by the inner wall surface can enter the light-receiving lens; it does not mean that no inner wall surface should be present over an infinitely long distance. In other words, there is no problem having an inner wall surface at a distance where the stray light caused by the inner wall surface does not affect the light-receiving lens.

In the Raman spectroscopic analyzer having the previously described configuration, the light beam generated from the light source converges on the predetermined position within the sample-passing unit and is cast into the fluid sample passing through the sample-passing unit. When the light beam is cast from the light source, scattered light is generated from the sample. Among the light scattered in the longitudinal direction of the sample-passing unit, the light scattered on the side where the light-receiving unit is placed is received by this light-receiving unit, and a Raman scattering spectrum is created by an appropriate analyzing system. Furthermore, the kinds and quantities of the substances contained in the sample are determined by an analysis of the Raman scattering spectrum.

In the Raman spectroscopic analyzer according to the present invention, the light-receiving unit is placed within the sample-passing unit, at a distance in the longitudinal direction of the sample-passing unit from the predetermined position where the light beam cast into the sample converges. In other words, the visual field of the light-receiving unit is directed in the longitudinal direction, with the predetermined position at its center. Therefore, if a portion of the light beam generated from the light source is scattered and directed onto the inner wall surface of the sample-passing unit, the thereby reflected light is prevented from directly entering the light-receiving unit. Thus, in the Raman spectroscopic analyzer according to the present invention, among the scattered light which enters the light-receiving unit, the portion which enters this unit after being reflected by the inner wall surface opposite to this unit is eliminated, so that the amount of noise which occurs in the Raman spectroscopic measurement due to the scattering of the excitation light is considerably reduced.

If the beam-casting unit and the light-receiving unit are independently constructed, the relative position of the beam-casting unit and the light-receiving unit easily changes, which causes a misalignment of the visual field of the light-receiving unit from the converging position of the incident beam and consequently lowers the detection efficiency of the Raman-scattered light.

Accordingly, the beam-casting unit and the light-receiving unit should preferably be integrally constructed. This construction prevents the unwanted change in the relative position of those units.

As for the arrangement of the beam-casting unit and the light-receiving unit in the Raman spectroscopic measurement for a fluid sample passing through a pipe, there are two possible forms, as shown in FIGS. 2A and 2B.

In the first form, as shown in FIG. 2A, the optical axis of the excitation light cast from the beam-casting unit 201 onto the predetermined position 202 of the sample fluid within the pipe 204 (excitation light axis) orthogonally intersects with that of the scattered light directed from the predetermined position 202 toward the light-receiving unit 203 (light-receiving axis). In the second form, as shown in FIG. 29, the excitation light axis and the light-receiving axis are coaxially arranged.

If the sample-passing unit is at a certain distance from the light source, a light guide (e.g. optical fiber) for propagating the light beam generated from the light source may be used. In the Raman scattering, in addition to the forward or backward scattering along the excitation light axis, the scattering of light also occurs in the direction perpendicular to the direction of polarization of the light cast into the sample. Commonly used optical fibers cannot maintain the direction of polarization of the propagated light, so that a variation occurs in the direction in which the Raman-scattered light is generated.

Accordingly, in the case where the excitation light axis orthogonally intersects with the light-receiving axis as shown in FIG. 2A, if a light guide is used in the beam-casting unit, a polarization-maintaining light guide (e.g. polarization-maintaining optical fiber) should preferably be used. By this system, the Raman-scattered light can be detected with a consistent intensity.

In the case where the excitation light axis and the light-receiving axis are coaxially arranged as shown in FIG. 2B, even if a common type of light guide (e.g. multimode optical fiber, including the one used for energy transmission) is used, the Raman-scattered light can be received with the same degree of consistency as in the case where the polarization-maintaining light guide is used.

The polarization-maintaining light guide should preferably maintain the plane of polarization of the light beam in a perpendicular direction to the longitudinal direction. By this configuration, the Raman-scattered light is generated in the direction where the light-receiving unit is placed, so that the detection intensity of the Raman-scattered light is increased.

Advantageous Effects of the Invention

In the Raman spectroscopic analyzer according to the present invention, if a portion of the light beam generated from the light source is scattered and directed onto the inner wall surface of the sample-passing unit, that light is prevented from directly entering the light-receiving unit, since the light-receiving unit is placed within the sample-passing unit and at a distance in the longitudinal direction of the sample-passing unit from the converging position of the incident beam. Therefore, the amount of noise which occurs due to the scattering of the excitation light is considerably reduced.

DESCRIPTION OF EMBODIMENTS

Figure 1:
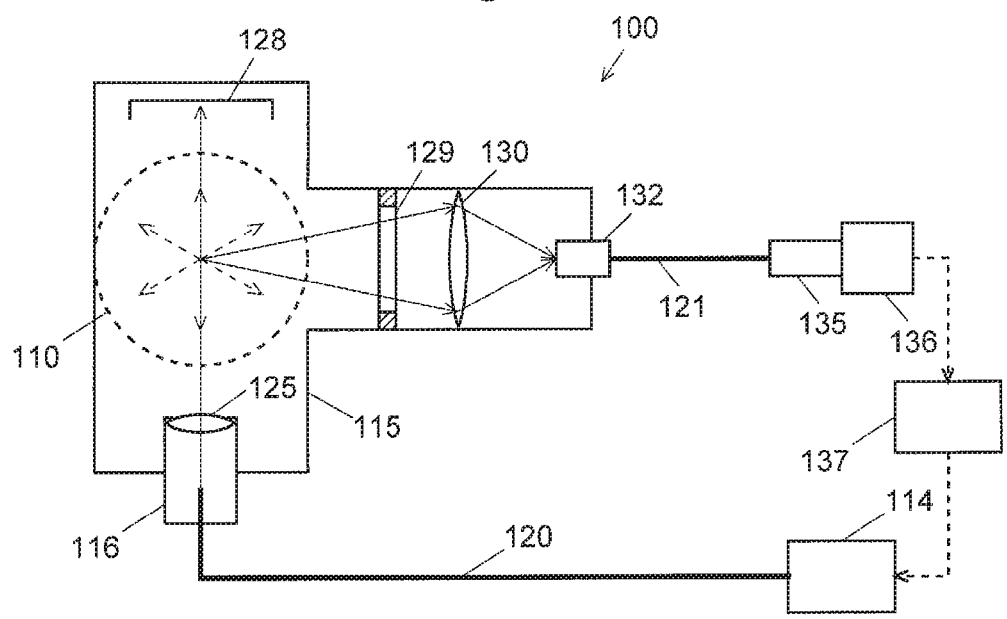
FIG. 1 is a diagram illustrating the schematic configuration of a conventional gas component analyzer.
Figure 2A:
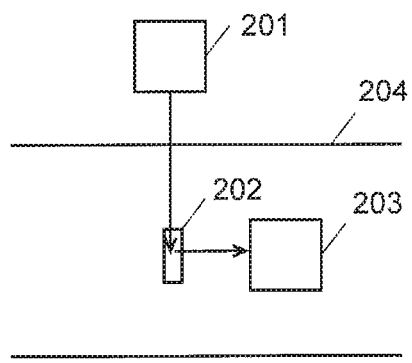
FIGS. 2A and 2B are schematic arrangement diagrams illustrating two examples of the arrangement of the beam-casting unit and the light-receiving unit.
Figure 2B:
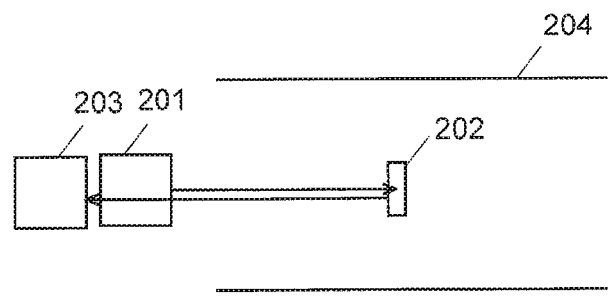
Figure 3:
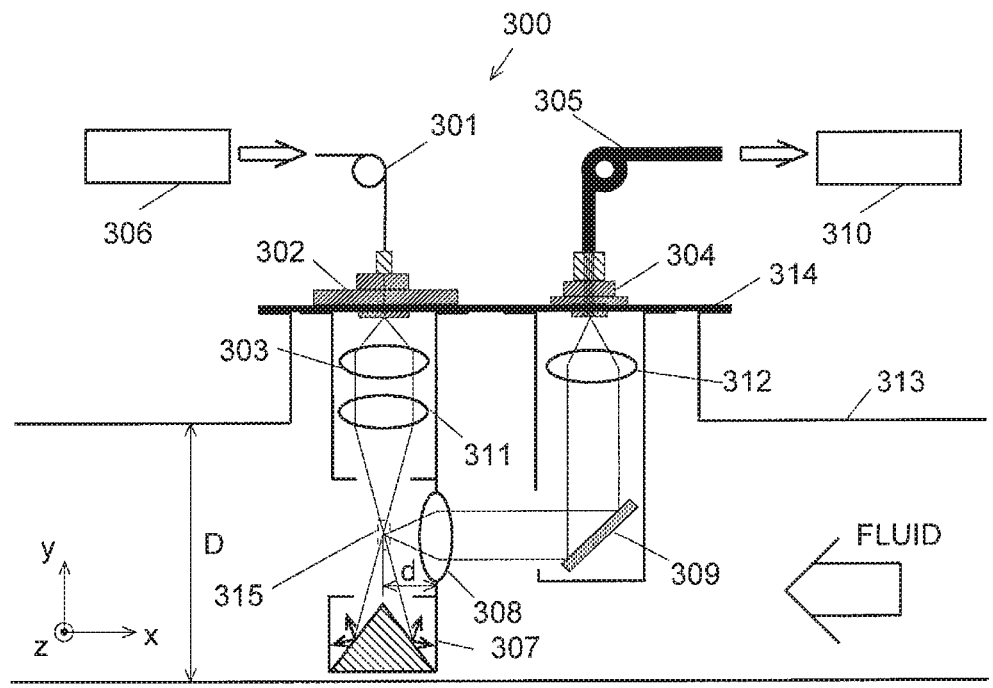
FIG. 3 is a schematic configuration diagram of a Raman spectroscopic analyzer as the first embodiment of the present invention.

A Raman spectroscopic analyzer as the first embodiment of the present invention is described with reference to FIG. 3. The Raman spectroscopic analyzer 300 of the first embodiment includes, a laser light source 306 for supplying the excitation light, a pipe 313 (sample-passing unit) for passing a fluid sample, a spectrometer 310 for detecting the scattered light from the fluid sample, a beam-casting unit and a light-receiving unit. The Raman spectroscopic analyzer 300 of the first embodiment is an example of the arrangement in which the excitation light axis orthogonally intersects with the light-receiving axis.

As the laser light source 306, a laser which generates visible light is used. For example, a solid laser (e.g. YAG laser or $YVO_4$ laser) or gas laser (e.g. Ar laser) can be used.

The excitation light generated from the laser light source 306 has a specific plane of polarization, such as the linear polarization. This light is introduced into the pipe 313 throb an optical fiber 301 connected to this pipe 313 by a connector 302. Then, the excitation light is collimated by a first entrance lens 303 and is converged into a central region of a Raman-scattered light measurement area 315 (this region is called the "predetermined position") by a second entrance lens 311. The Raman-scattered light measurement area 315 is located near the central axis of the tubular pipe 313. The excitation light is converged from a direction (y direction) perpendicular to the longitudinal direction (x direction) of the pipe 313 into the central region of the Raman-scattered light measurement area 315. The optical fiber 301, first entrance lens 303 and second entrance lens 311 constitute the beam-casting unit. Although the present description deals with the case where the excitation light generated from the laser light source 306 has a specific plane of polarization (e.g. linear polarization), the present embodiment is not limited to this case; it is possible to use a light source that generates light with no specific plane of polarization.

After passing through the Raman-scattered light measurement area 315, the excitation light is trapped by a beam trap 307 and thereby absorbed. This prevents the excitation light from being directed onto the inner wall surface of the pipe 313.

The Raman-scattered light generated within the Raman-scattered light measurement area 315 by the excitation light cast into the fluid sample passing through the pipe 313 in the longitudinal direction of this pipe is collimated parallel to the longitudinal direction (x direction) of the pipe 313 by a light-receiving lens 308 placed next to the predetermined position of the Raman-scattered light measurement area 315 at distance d in the longitudinal direction (x direction) of the pipe 313. The collimated beam is redirected by a mirror 309 into the perpendicular direction (y direction) to the longitudinal direction (x direction).

Since the light-receiving lens 308 is placed in the longitudinal direction (x direction) of the pipe 313, no inner wall surface of the pipe 313 is present opposite to the light-receiving lens 308 across the predetermined position of the Raman-scattered light measurement area 315. Therefore, the stray light from the inner wall surface of the pipe 313 is prevented from entering the visual field of the light-receiving lens 308 to be received.

Subsequently, the Raman-scattered is introduced through a converging lens 312 into a fiber bundle 305 connected to the pipe 313 by a connector 304. The fiber bundle 305 comprises a bundle of optical fibers. These optical fibers are arranged in a rectangular form with the longer side extending in the x direction, which form corresponds to a rectangular area whose longer side extends in the y direction in the Raman-scattered light measurement 315. The light-receiving lens 308, mirror 309, converging lens 312 and fiber bundle 305 constitute the light-receiving unit.

The fiber bundle 305 can receive light from multiple points within the rectangular area in the Raman-scattered light measurement 315. The use of the fiber bundle 305 enables an efficient reception of the faint Raman-scattered light. In other words, the light-receiving unit detects the scattered light originating from the Raman-scattered light measurement area 315 (which is a rectangular area whose center lies on the predetermined position, with the longer side extending in the perpendicular direction to the longitudinal direction of the sample-passing unit).

The Raman-scattered light is extracted through the fiber bundle 305 to the outside of the pipe 313 and enters the spectrometer 310. In the spectrometer 310, the detected Raman-scattered light is separated into component wavelengths, and a wavelength dispersion spectrum of the Raman scattering is obtained. Using this spectrum, the Raman spectroscopic analysis of the fluid sample can be performed.

The optical fiber 301, first entrance lens 303 and second entrance lens 311 constituting the beam-casting unit are connected to the pipe 313 by the connector 302, while the light-receiving lens 308, mirror 309, converging lens 312 and fiber bundle 305 constituting the light-receiving unit are connected to the pipe 313 by the connector 304, with the beam-casting unit and the light-receiving unit sharing a flat plate 314 in the outer wall surface of the pipe 313. Since the beam-casting unit and the light-receiving unit are integrally fixed to the same flat plate 314 in the outer wall surface of the pipe 313, an unwanted change in the relative position of the beam-casting unit and the light-receiving unit does not easily occur. Thus, a Raman spectroscopic analyzer which is highly resistant to vibration and allows for a low frequency of maintenance is obtained.

With the Raman spectroscopic analyzer according to the present invention, a polarized Raman spectroscopic analysis can be performed. In general, Raman-scattered light is generated in the perpendicular direction to the polarizing direction. Therefore, in the case of a system configured to detect side-scattered light as shown in FIG. 3, if the plane of polarization of the excitation light is not controlled, the detection intensity varies depending on the polarizing direction of the excitation light converging on the Raman-scattered light detection area 315. To overcome this problem, a polarization-maintaining fiber capable of maintaining the polarizing direction of the light can be used as the optical fiber 301 which propagates the excitation light. In this case, the excitation light having a specific plane of polarization (e.g. linear polarization) generated from the laser light source 306 maintains the same plane of polarization before and after passing through the optical fiber 301 until it is converged on the Raman-scattered light detection area 315. By aligning this plane of polarization parallel to the light-receiving lens 308, the Raman-scattered light generated in the perpendicular direction to the direction of polarization can be consistently received.

Figure 4:
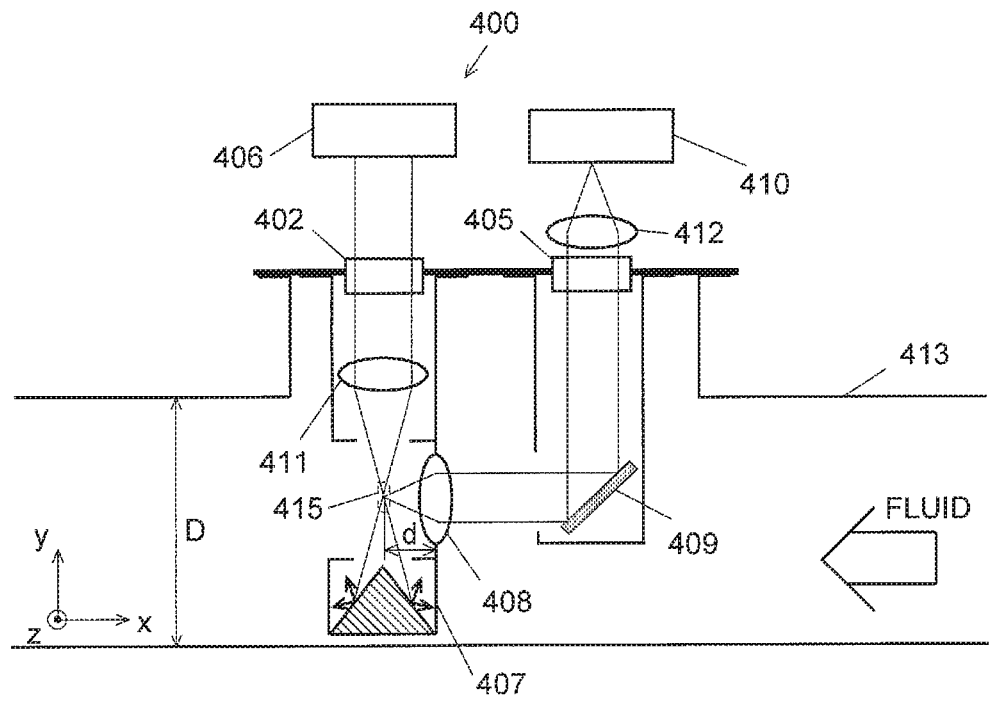
FIG. 4 is a schematic configuration diagram of a Raman spectroscopic analyzer as the second embodiment of the present invention.

A Raman spectroscopic analyzer as the second embodiment of the present invention is described with reference to FIG. 4. The Raman spectroscopic analyzer 400 of the second embodiment includes a laser light source 406 for supplying the excitation light, a pipe 413 (sample-passing unit) for passing a fluid sample, a spectrometer 410 for detecting the scattered light from the fluid sample, a beam-casting unit and a light-receiving unit. The Raman spectroscopic analyzer 400 of the second embodiment is an example of the arrangement in which the excitation light axis orthogonally intersects with the light-receiving axis.

As the laser light source 406, the same type as the laser light source 306 is used.

The excitation light generated from the laser light source 406 enters the pipe 413 through a window 402. Then, this excitation light is converged by a condensing lens 411 into a central region (predetermined position) of a Raman-scattered light measurement area 415. The Raman-scattered light measurement area 415 is located near the central axis of the tubular pipe 413. The excitation light is converged from a direction (y direction) perpendicular to the longitudinal direction (x direction) of the pipe 413 into the Raman-scattered light measurement area 415. The condensing lens 411 constitutes the beam-casting unit.

After passing through the Raman-scattered light measurement a 415, the excitation light is trapped by a beam trap 407 so as to prevent the excitation light from being directed onto the inner wall surface of the pipe 413.

The Raman-scattered light generated from the fluid sample passing through the pipe 413 within the Raman-scattered light measurement area 415 is collimated parallel to the longitudinal direction (x direction) of the pipe 413 by a light-receiving lens 408 placed next to the Raman-scattered light measurement area 415 at distance d in the longitudinal direction (x direction) of the pipe 413. The collimated beam is redirected by a mirror 409 into the perpendicular direction (y direction) to the longitudinal direction (x direction). The redirected Raman-scatter light is extracted through a window 405 to the outside of the pipe 413 and enters the spectrometer 410 through a converging lens 412. The light-receiving lens 408, mirror 409 and converging lens 412 constitute the light-receiving unit.

In the spectrometer 410, the detected Raman-scattered light is separated into component wavelengths, and a wavelength dispersion spectrum of the Raman-scattered light is obtained. Using this spectrum, the Raman spectroscopic analysis of the fluid sample can be performed.

The system of the second embodiment is configured so that the Raman-scattered light generated in the Raman-scattered light measurement area 415 is directly introduced into the spectrometer 410. Unlike the system using a common type of optical fiber through which only a faint Raman-scattered light originating from a single point within the Raman-scattered light measurement area 415 is received, the present system can receive the Raman-scattered light from the entire area and efficiently detect the faint Raman-scattered light.

A Raman spectroscopic analyzer as the third embodiment of the present invention is described with reference to FIG. 5. The Raman spectroscopic analyzer 500 of the third embodiment includes: a laser light source 506 for supplying the excitation light; an optical fiber 501; an illumination beam-converging optical system 507 for converging the excitation light into a fluid sample; a reflecting optical system 505 including a reflection mirror 503 for reflecting the excitation light; a pipe 513 (sample-passing unit) for passing a fluid sample; a detection light-converging optical system 504 for converging the Raman-scattered light, comprising a collimating unit (light-receiving lens) 504A or 504C and a converging unit 504B; and a spectrometer 510 for detecting the scattered light from the fluid sample. The Raman spectroscopic analyzer 500 of the third embodiment is an example in which the excitation light axis and the light-receiving axis are coaxially arranged.

Figure 5:
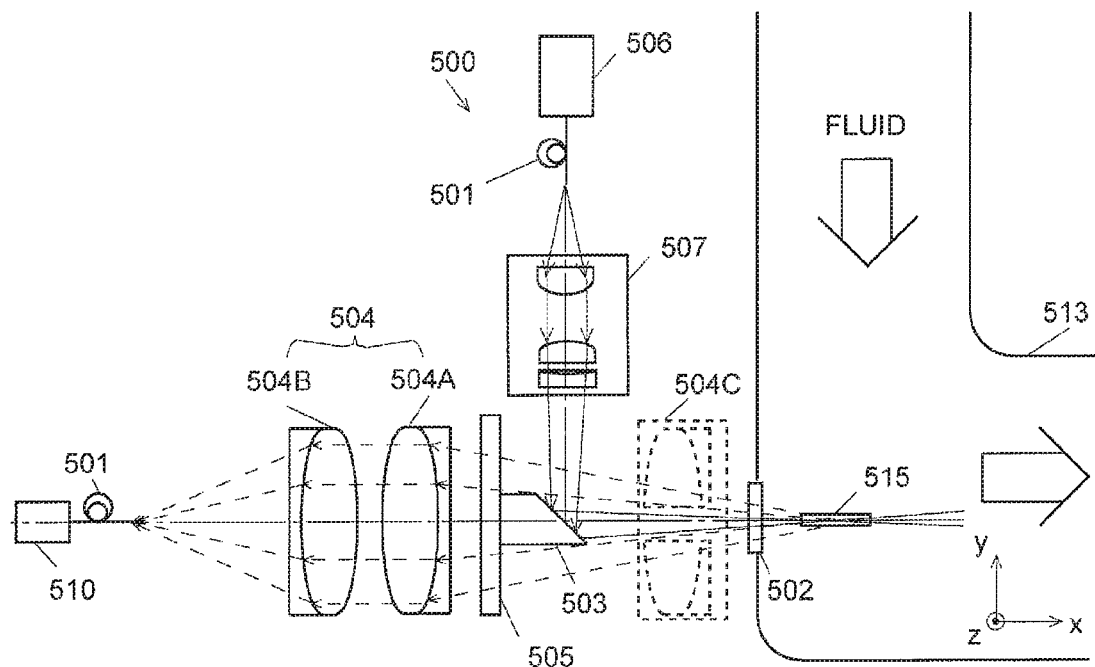
FIG. 5 is a schematic configuration diagram of a Raman spectroscopic analyzer as the third embodiment of the present invention.

The pipe (sample-passing unit) 513 shown in FIG. 5 is L-shaped, with a window 502 provided in the bend section at such a position where the line of sight through the window is aligned with the longitudinal direction (x direction) of the tubular body of the pipe (sample-passing unit). By using such a pipe, a coaxial arrangement of the excitation light axis and the light-receiving axis can be realized.

As the laser light source 506, the same type as the laser light source 306 is used.

The excitation light generated from the laser light source 506 enters the pipe 513 through the window 502. Then, this excitation light is converged by the illumination beam-converging optical system 507 into a central region (predetermined position) in a Raman-scattered light measurement area 515. The Raman-scattered light measurement area 515 is located near the central axis of the tubular pipe 513. The excitation light is converged from the longitudinal direction (x direction) of the pipe 513 into the Raman-scattered light measurement area 515.

Among the Raman-scattered light generated from the fluid sample passing through the pipe 513 within the Raman-scattered light measurement area 515, the back-scattered component passes through the window 502, the detection light-converging optical system 504 comprising the collimating unit (light-receiving lens) 504A or 504C and the converging unit 504B, as well as the optical fiber 501, to eventually enter the spectrometer 510.

In the spectrometer 510, the detected Raman-scattered light is separated into component wavelengths, and a wavelength dispersion spectrum of the Raman-scattered is obtained. Using this spectrum, the Raman spectroscopic analysis of the fluid sample can be performed.

The system of the third embodiment is configured so that the back-scattered component of the Raman-scattered light generated in the Raman-scattered light measurement area 515 is made to enter the spectrometer 510. The excitation light axis and the light-receiving axis are coaxially arranged. Such an arrangement can also satisfy the condition that no inner wall surface of the pipe 513 is present opposite to the detection light-converging optical system 504 across the predetermined position in the Raman-scattered light measurement area 515. Therefore, the stray light from the inner wall surface of the pipe 513 is prevented from entering the detection light-converging optical system 504 to be received.

REFERENCE SIGNS LIST

100 . . . Gas Component Analyzer
110 . . . Sample-Passing Unit
114 . . . Laser-Casting Device
115 . . . Measurement Chamber
116 . . . Light-Casting Means
120 . . . First Optical Fiber
121 . . . Second Optical Fiber
125 . . . Lens
128 . . . Damper
129 . . . Light-Passing Window
130 . . . Condensing Lens
132 . . . Light-Receiving Unit
135 . . . Spectrometer
136 . . . CCD Camera
137 . . . Controller
201 . . . Beam-Casting Unit
202 . . . Predetermined Position 203 . . . Light-Receiving Unit
300, 400, 500 . . . Raman Spectroscopic Analyzer
301, 501 . . . Optical Fiber
302, 304 . . . Connector
303, 308, 311, 312, 408, 411, 412 . . . Lens
305 . . . Fiber Bundle
306, 406, 506 . . . Laser Light Source
307, 407 . . . Beam Trap
309, 409, 503 . . . Mirror
310 410, 510 . . . Spectrometer
313, 413, 513 . . . Pipe
314 . . . Flat Plate
315, 415, 515 . . . Raman-Scattered Light Measurement Area
402, 405, 502 . . . Window
504A, 504C . . . Collimating Unit
504 505, 507 . . . Optical System
504B . . . Converging Unit

The invention claimed is:

1. A Raman spectroscopic analyzer, comprising:
   a) a sample-passing unit in a form of a tube, for passing a fluid sample in a longitudinal direction of the tube;
   b) a beam-casting unit for converging a light beam generated by a light source on a predetermined position within the sample-passing unit; and
   c) a light-receiving unit placed at a distance in the longitudinal direction from the predetermined position, including a light-receiving lens for receiving scattered light emitted from the fluid sample.

2. The Raman spectroscopic analyzer according to claim 1, wherein no inner wall surface of the sample-passing unit is present opposite to the light-receiving lens across the predetermined position.

3. The Raman spectroscopic analyzer according to claim 1, wherein the beam-casting unit is arranged so as to converge the light beam on the predetermined position from a perpendicular direction to the longitudinal direction.

4. The Raman spectroscopic analyzer according to claim 1, wherein the sample-passing unit has a bend section and a straight section connected to the bend section, and the beam-converging unit and the light-receiving unit are coaxially provided in a direction from the bend section to the straight section.

5. The Raman spectroscopic analyzer according to claim 1, wherein the light-receiving unit detects the scattered light generated from a rectangular area whose center lies on the predetermined position, with a longer side of the rectangular area extending in a perpendicular direction to the longitudinal direction of the sample-passing unit.

6. The Raman spectroscopic analyzer according to claim 1, wherein the light-receiving unit includes a fiber bundle.

7. The Raman spectroscopic analyzer according to claim 1, wherein the beam-casting unit includes a polarization-maintaining fiber.

8. The Raman spectroscopic analyzer according to claim 1, wherein the beam-casting unit and the light-receiving unit are integrally fixed to a flat plate in an outer wall surface of the sample-passing unit.

\* \* \* \* \*